(12) United States Patent
Colle

(10) Patent No.: US 7,583,377 B2
(45) Date of Patent: Sep. 1, 2009

(54) OPTOELECTRONIC PROCESS AND A DEVICE FOR INSPECTION OF AN AREA OF REVOLUTION OF A RECEPTACLE

(75) Inventor: Olivier Colle, Oullins (FR)

(73) Assignee: Tiama, Montagny (FR)

( * ) Notice: Subject to any disclaimer, the term of this patent is extended or adjusted under 35 U.S.C. 154(b) by 61 days.

(21) Appl. No.: 10/575,164

(22) PCT Filed: Oct. 13, 2004

(86) PCT No.: PCT/FR2004/002595

§ 371 (c)(1),
(2), (4) Date: May 11, 2007

(87) PCT Pub. No.: WO2005/038444

PCT Pub. Date: Apr. 28, 2005

(65) Prior Publication Data

US 2008/0062416 A1    Mar. 13, 2008

(30) Foreign Application Priority Data

Oct. 13, 2003   (FR)   ................................. 03 11951

(51) Int. Cl.
*G01N 21/90* (2006.01)

(52) U.S. Cl. .................... 356/239.5; 382/142; 348/127; 250/223 B

(58) Field of Classification Search .............. 356/240.1, 356/239.4, 239.5
See application file for complete search history.

(56) References Cited

U.S. PATENT DOCUMENTS 3,708,680 A * 1/1973 Calhoun ................. 250/223 B
3,980,890 A * 9/1976 Heckrodt et al. ........ 250/559.28
4,293,219 A * 10/1981 Ducloux ................... 356/239.4
4,304,995 A * 12/1981 Huttunen et al. ........ 250/339.06
4,454,542 A * 6/1984 Miyazawa ................... 348/127
4,914,289 A * 4/1990 Nguyen et al. ........... 250/223 B
5,095,204 A * 3/1992 Novini .................... 250/223 B
5,430,538 A   7/1995 Kobayashi

FOREIGN PATENT DOCUMENTS

DE      299 07 762    11/1999
EP      0 387 930      9/1990
EP      0 566 397     10/1993

* cited by examiner

*Primary Examiner*—Gregory J Toatley, Jr.
*Assistant Examiner*—Rebecca C Slomski
(74) *Attorney, Agent, or Firm*—Clark & Brody

(57) ABSTRACT

An optoelectronic process for inspection of an area of revolution of a receptacle presenting an axis of revolution, includes:
  illumination of the surface to be inspected using a lighting system presenting an axis of revolution that is located in the extension of the axis of revolution of the receptacle,
  formation of an image of the inspected surface using a camera, and analysis of the image formed with a view to checking the characteristics of the surface to be inspected.

The illumination is over at least three angular sectors, each emitting a given radiation spectrum that is separate from all the spectra of the other sectors. Only the light rays returned by the surface to be inspected are selected and one of the said given radiation spectra are presented to eliminate the parasitic light rays whose radiation spectrum does not correspond to that selected for the said angular sector.

11 Claims, 2 Drawing Sheets

OPTOELECTRONIC PROCESS AND A DEVICE FOR INSPECTION OF AN AREA OF REVOLUTION OF A RECEPTACLE

This present invention concerns the technical area of the optoelectronic inspection of hollow objects or receptacles, in the general sense, of a transparent or translucid character in particular, such as, for example, bottles, pots or glass containers, with a view to checking or evaluating the characteristics presented by such a receptacle.

The subject of the invention has a particularly advantageous application to detect surface faults in the finish of a transparent or translucid object.

The subject of the invention has another application that aims to detect surface lifting faults corresponding to the presence of flashing or smearing on the internal part of the edge of the finish of a receptacle.

From previous designs, one is familiar with many technical solutions for the inspection of receptacles, with a view to finding faults in particular. In general, an inspection device includes a lighting system providing an incident light beam of revolution illuminating the surface of the finish of the receptacle. Such an inspection device also includes a system for the formation of an image of the surface of the finish. In particular, such a system includes a camera and a lens positioned to collect the light beams reflected by the finish of the receptacle. The presence of a fault disrupts the reflection of the light, so that analysis of the video signal delivered by the camera enables the presence of the said fault to be detected.

Such an inspection device has a major disadvantage associated with the problem of parasitic reflections of the incident light rays coming, in particular, from the bottom and the wall of the receptacle. These light parasites, which appear on the image, complicate the processing of the image in order to determine the actual presence of faults or not. There is a real risk that a receptacle may be incorrectly classified as defective because of such parasites. On the other hand, and more seriously, these light parasites are sometimes capable of preventing the detection of faults present on the receptacle.

Document DE 299 07 762 describes a device that aims to detect faults appearing on the neck of a receptacle by using at least two light sources of different colour. For example, the neck of a receptacle is illuminated by three concentric light beams coloured red, green and blue, each illuminating a different annular sector. It should be noted that the lighting angles of the light sources are different, so as to obtain a suitable angle of reflection of the incident beams covering all the surface of the finish inspected.

It turns out that the positioning of the light sources is relatively difficult to achieve correctly. Apart from this, the principle of operation of such a device leads to the appearance of parasitic reflections, which reduces the quality of fault detection on the receptacles.

There is therefore a need to find a method for optoelectronic inspection of the area of revolution of a hollow object, designed to eliminate light parasites so as to make the procedure for the inspection of such receptacles a reliable one.

The subject of the invention therefore aims to propose an optoelectronic process for the inspection of an area of revolution of a receptacle, which includes the following stages:
  illumination of the surface to be inspected using a lighting system that has an axis of revolution located in the extension of the axis of revolution of the receptacle, and that includes at least three given radiation spectra,
  formation of an image of the surface to be inspected, using a camera,
  analysis of the image formed, with a view to checking the characteristics of the surface to be inspected.

This process consists of:
  illuminating over at least three angular sectors, each emitting a given radiation spectrum that is separate from all the spectra of the other sectors,
  and for each angular sector of the surface to be inspected, formation of an image by selecting only the light rays returned by the surface and presenting one of the said given radiation spectra, so as to eliminate the parasitic light rays whose radiation spectrum does not correspond to that selected for the said angular sector.

According to a preferred implementation variant, the process according to the invention consists of forming an image for each angular sector of the surface to be inspected by selecting only the light rays returned by the surface and coming from an angular sector of the lighting system located on the same side as the said angular sector of the surface to be inspected in relation to the axis of revolution.

According to this preferred implementation variant, the parasites due to the light coming from the opposite part of the source are removed, since only the light coming from the adjacent part of the source is taken into account for inspection of the surface of the receptacle.

According to another implementation variant, the process according to the invention consists of forming an image for each angular sector of the surface to be inspected, by selecting only the light rays returned by the surface and coming from an angular sector of the lighting system located on the opposite side of the said angular sector in relation to the axis of revolution.

Advantageously, the process consists of illuminating the surface to be inspected in angular sectors of equal value.

Again advantageously, the process consists of illuminating by means of radiation spectra that are each of a given colour.

One application of the process according to the invention consists of analysing the image formed, in order to determine flashing or surface faults on the finish of a receptacle.

Another objective of the invention is to propose an inspection device that includes:
  a lighting system with an axis of revolution located in the extension of the axis of revolution of the receptacle, and that includes at least three given radiation spectra,
  and a system for the formation of an image of the surface to be inspected, that includes a camera and resources for analysis of the image with a view to checking the characteristics of the surface to be inspected.

According to the invention:
  the lighting system has a lighting surface that is divided into at least three angular sectors, each emitting a given radiation spectrum and separate from all the spectra of the other sectors,
  for each angular sector of the surface to be inspected, the image formation system forms an image by selecting only the light rays returned by the surface and presenting one of the said given radiation spectra, so as to eliminate the parasitic light rays whose radiation spectrum does not correspond to that selected for the said angular sector.

According to a preferred implementation variant, the device includes an image formation system which, for each angular sector of the surface to be inspected, forms an image by selecting only the light rays returned by the surface and coming from an angular sector of the lighting system located on the same side as the said angular sector of the surface to be inspected, in relation to the axis of revolution.

According to another implementation variant, the device includes an image formation system which, for each angular sector of the surface to be inspected, forms an image by selecting only the light rays returned by the surface and coming from an angular sector of the lighting system located on the opposite side of the said angular sector of the surface to be inspected, in relation to the axis of revolution.

According to a first form of implementation of the lighting system, the said system includes an annular source presenting all of the given radiation spectra, and a series of at least three filters placed between the annular source and the surface to be inspected, each lying on an angular sector, and each filter presenting a given transmission spectrum that is separate from that of the other filters.

According to a second form of implementation of the lighting system, the said system includes a series of elementary light sources, such as electroluminescent diodes, divided over at least three angular sectors and emitting a light spectrum that is different for each angular sector.

According to a first form of implementation of the image formation system, the said system includes a series of at least three filters interposed between the camera and the surface to be inspected, each lying on an angular sector, and each filter presenting a given transmission spectrum separate from that of the other filters.

According to a second form of implementation of the image formation system, the said system includes resources for processing the signals delivered by a colour camera so as to obtain, for each angular sector of the surface to be inspected, a signal that is representative of a given radiation spectrum.

Diverse other characteristics will emerge from the description provided below with reference to the appended drawings which show, by way of non-limiting examples, various forms of implementation of the subject of the invention.

Figure 1:
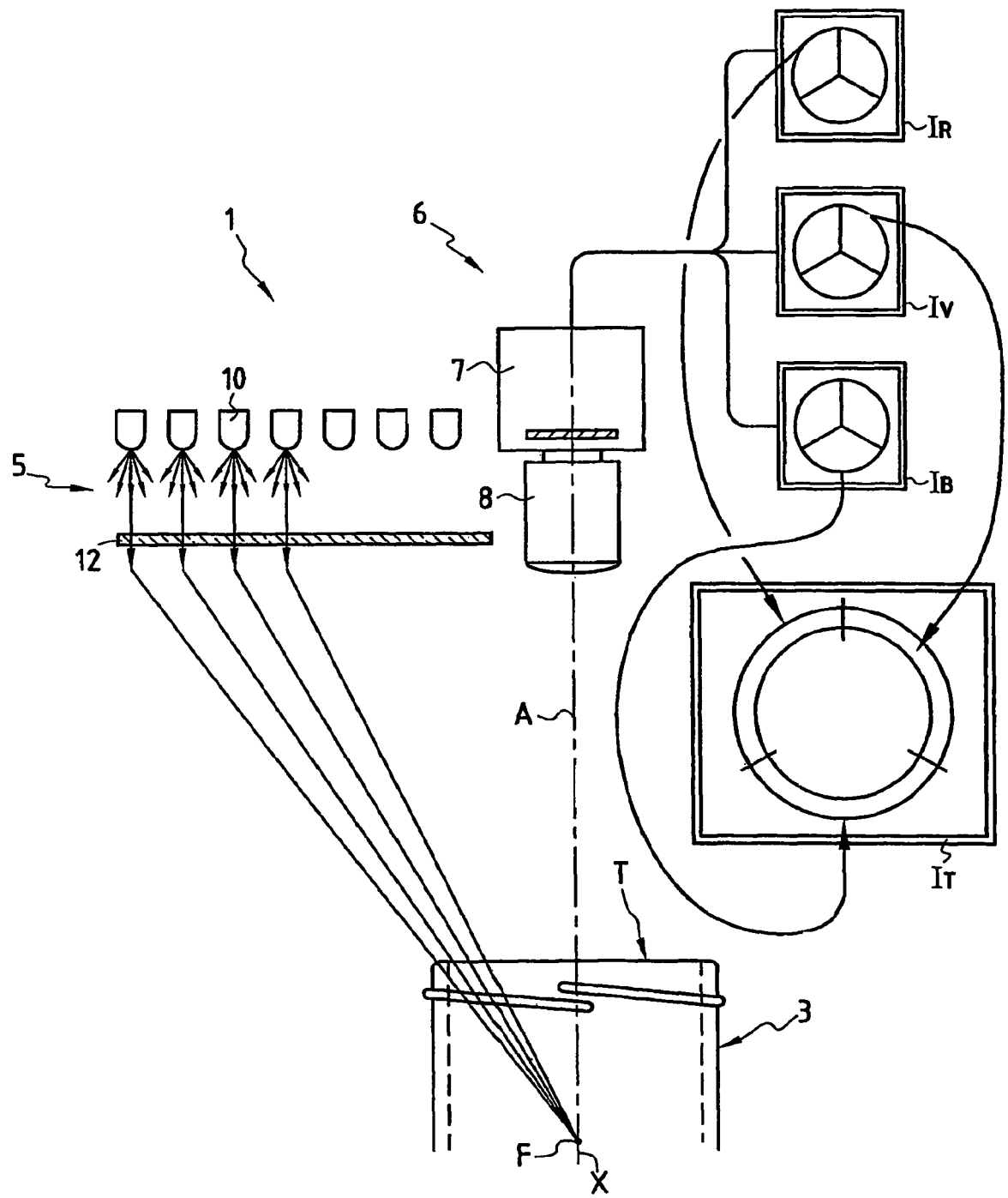
FIG. 1 is a view in elevation of an inspection device according to the invention implemented according to a first form of implementation.
Figure 2:
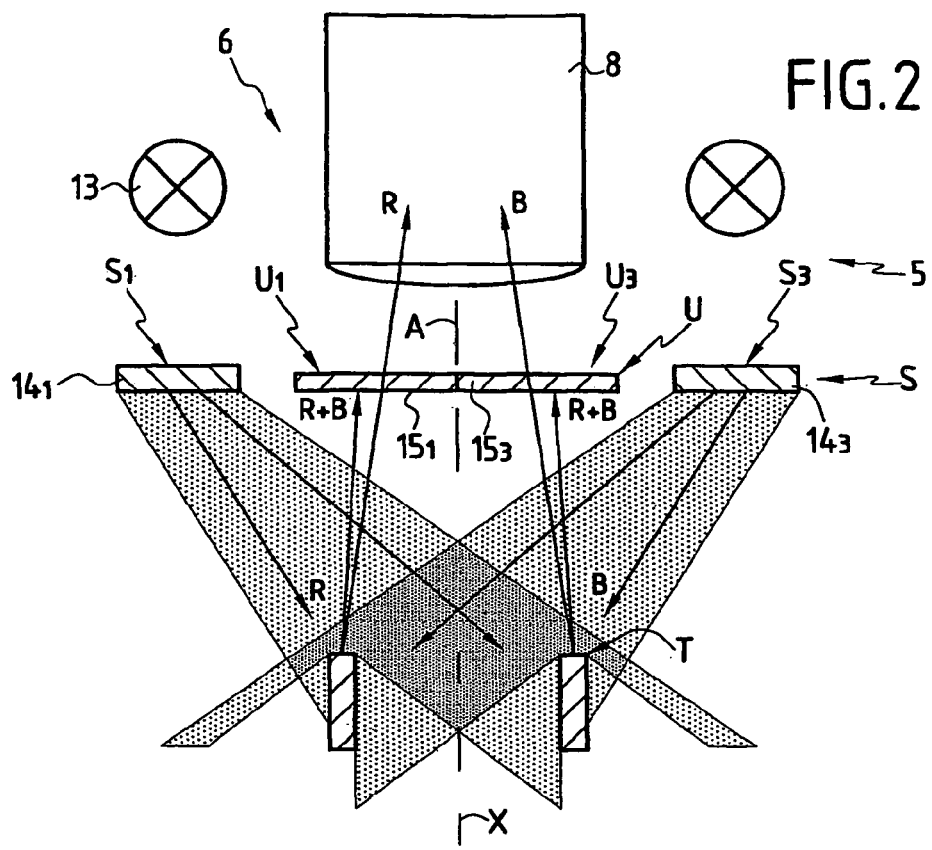
FIG. 2 is a diagrammatic view in elevation explaining the principle of the inspection device of the invention according to a second form of implementation.
Figure 3:
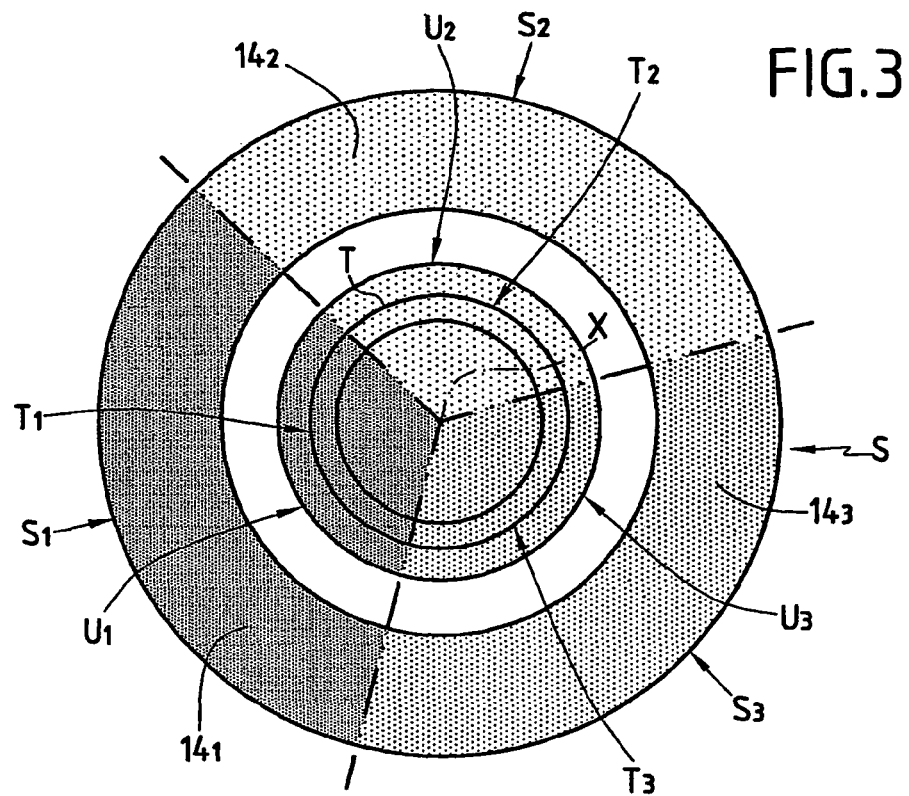
FIG. 3 is a diagrammatic plan view explaining the principle of the inspection device of the invention illustrated in FIG. 2.

As emerges more precisely from FIGS. 1 to 3, the subject of the invention concerns an optoelectronic device 1 designed to inspect an area of revolution T of a receptacle 3 in the general sense. This receptacle 3 which has an axis of symmetry or of revolution X, preferably, though not exclusively, has a transparent or translucid character. Such an inspection arrangement 1 includes a system 5 for illuminating the surface to be inspected T and a system 6 to form an image of the surface to be inspected T. Such an image formation system 6 includes, in particular, a camera 7 equipped with a lens 8 and connected to a processing and analysis unit designed to analyse the video signal delivered by the camera with a view to checking the characteristics of the surface to be inspected T. The processing and analysis unit will not be described more precisely to the extent that it does not form part of the subject of the invention and is already familiar to the professional engineer.

As emerges more precisely from FIGS. 2 and 3, the lighting system 5 presents a lighting surface S having an axis of revolution A, and presenting all forms and dimensions of revolution including cylindrical, conical, hemispherical or plane, as illustrated in the figures. This lighting surface S is divided into at least three angular sectors $S_1$, $S_2$, $S_3$ each emitting a given radiation spectrum, separate from all the spectra of the other sectors. In other words, to each angular sector $S_1$, $S_2$, $S_3$ is attributed a given radiation spectrum which is separate from the other spectra assigned to the other sectors. Thus, the radiation spectra have no common value, meaning that they do not overlap. Preferably, it can be arranged that each radiation spectrum corresponds to a given colour such as red, green, blue or yellow, for example. In the example illustrated in FIGS. 2 and 3, the angular sectors $S_1$, $S_2$, $S_3$ emit radiation spectra respectively in red R, green V and blue B. It should be noted that, in the sense of the invention, each angular sector $S_1$, $S_2$, $S_3$ of the lighting surface S includes a given radiation spectrum, so that at each point of the angular sectors $S_1$, $S_2$, $S_3$ the radiation spectrum emitted is separate from the radiation spectrum emitted in the vicinity of an opposite or symmetrical point taken in relation to the axis of revolution A.

As described above, the lighting system 5 is used to illuminate the surface to be inspected T over at least, and in the example illustrated three, angular sectors $T_1$, $T_2$, $T_3$. In other words, the surface to be inspected T is divided into at least three angular sectors sectors $T_1$, $T_2$, $T_3$ each receiving at least one given radiation spectrum. It should be noted that the receptacle 3 is positioned so that its axis of revolution X is located in the extension of the axis of revolution A of the lighting system. In the example illustrated in FIGS. 2 and 3, the angular sectors sectors $T_1$, $T_2$, $T_3$ of the finish surface T receive radiation spectra corresponding respectively to red R, green V and blue B. It should be understood that assigned to each angular sector sectors $T_1$, $T_2$, $T_3$ of the surface to be inspected T is a radiation spectrum that is separate from the other radiation spectra. Each angular sector sectors $T_1$, $T_2$, $T_3$ of the finish surface T preferably has an identical angular reach, namely 120° in the example illustrated. In the case where the surface to be inspected T is divided into four sectors, each of these has an angular reach of 90°.

According to a first implementation variant illustrated in FIG. 1, the lighting system 5 includes a series of elementary light sources 10, such as electroluminescent diodes, divided over three angular sectors $S_1$, $S_2$, $S_3$ and emitting a given radiation spectrum for each angular sector. In the example illustrated, it can be arranged, in each angular sector $S_1$, $S_2$, $S_3$ to mount diodes of a given colour, such as red, green or blue for example.

In the example illustrated in FIG. 1, concerning more particularly a device for the detection of surface faults, the lighting system 5 includes an optical system 12 placed between the elementary light sources 10 and the surface to be inspected T and designed to perform the convergence or focussing of the uniform light ring at a point of convergence F located on the axis of symmetry X of the receptacle. According to this example, the finish surface T to be inspected is therefore illuminated by a uniform and convergent incident light beam. Of course, the subject of the invention applies whatever the nature of the lighting. Thus, the light emitted in the direction of the receptacle can have very diverse characteristics, such as, for example, divergent or convergent, more or less extended, homogeneous, diffused, etc.

According to a second implementation variant illustrated more particularly in FIGS. 2 and 3, the lighting system 5 includes an annular light source 13 with an axis of revolution A and with all of the radiation spectra, and a series of filters $14_1$, $14_2$, $14_3$ placed between the annular source 13 and the surface to be inspected T. Each filter $14_1$, $14_2$, $14_3$ thus lies on a given angular sector $S_1$, $S_2$, $S_3$ of the lighting surface, and presents a given transmission spectrum that is separate from that of the other filters. In other words, each filter $14_1$, $14_2$, $14_3$ passes a given radiation spectrum and blocks the other radiation spectra. In the example concerned, each angular sector $S_1$, $S_2$, $S_3$ of the lighting surface S is fitted with a filter such that each of these allows the transmission of a different radiation spectrum, namely red R, green V, and blue B respectively.

According to another characteristic of the invention, for each angular sector sectors $T_1$, $T_2$, $T_3$ of the surface to be inspected T, the system 6 forms an image by selecting only the light rays returned by the surface T and presenting one of the said given radiation spectra, so as to eliminate the parasitic light rays whose radiation spectrum do not correspond to that selected for the said angular sector. In other words, for each angular sector sectors $T_1$, $T_2$, $T_3$ of the surface to be inspected T, the system 6 collects only the light rays returned by the surface to be inspected T and presenting, for each angular sector sectors $T_1$, $T_2$, $T_3$ of the surface to be inspected T, the radiation spectrum selected for or assigned to the said angular sector. It should be understood that each angular sector sectors $T_1$, $T_2$, $T_3$ of the surface to be inspected T can receive several radiation spectra. However, each radiation spectrum received by an angular sector sectors $T_1$, $T_2$, $T_3$ of the surface to be inspected T that is different from that assigned to the said angular sector is eliminated, since it is considered to be a light parasite.

As an example, FIG. 2 shows in particular that each of the angular sectors $T_1$, $T_3$ of the surface to be inspected T returns two radiation spectra, namely red R and blue B. However, for these angular sectors $T_1$, $T_3$, the image formation system 6 is designed to collect only the radiation spectra attributed to these sectors, namely respectively red R, and blue B.

In the example illustrated in FIGS. 2 and 3, selection of the radiation spectra for each angular sector of the finish surface T is achieved by the use of optical filters whose number and position are identical to the angular sectors of the surface to be inspected T. Thus filters $15_1$, $15_2$, $15_3$ are interposed between the camera 8 and the surface to be inspected T extending over an angular reach $U_1$, $U_2$, $U_3$ respectively corresponding to that of an angular sector sectors $T_1$, $T_2$, $T_3$ of the finish surface T. Each filter $15_1$, $15_2$, $15_3$ presents a given transmission spectrum that is separate from that of the other filters. In other words, each filter passes a given radiation spectrum and blocks the other radiation spectra. In the example illustrated in FIGS. 2 and 3, each angular sector $U_1$, $U_2$, $U_3$ of the surface of a filter is such that each of them allows the transmission of a different radiation spectrum, namely red R, green V, and blue B respectively.

FIG. 1 illustrates a second variant, namely electronic or software, to select the radiation spectra for each of the angular sectors of the said surface to be inspected, from amongst the beams returned by the surface to be inspected T. In this regard, the beams returned by the surface to be inspected T are collected by a colour camera whose associated analysis and processing unit is used to separate the radiation spectra, namely red, green and blue, for each angular sector of the surface to be inspected T. As illustrated, for each angular sector of the surface to be inspected T, an image is obtained, namely red $I_R$, green $I_V$ and blue $I_B$, whose combination allows an image $I_T$ of the surface inspected to be obtained, divided into angular sectors. For each of these angular sectors, the processing resources are used to obtain a signal that is representative of a given radiation spectrum separate from that of the other angular sectors. It should be noted that this software process performed on the signals delivered by the colour camera constitutes a process equivalent to that performed by the filters described in relation to FIGS. 2 and 3.

According to a preferred implementation example, each angular sector $S_1$, $S_2$, $S_3$ of the lighting system 5 is located on the same side, in relation to the axis of revolution X, as an angular sector of finish surface T, whose collected radiation spectrum corresponds to that of the adjacent angular sector $S_1$, $S_2$, $S_3$. Thus, as emerges from the example illustrated in FIGS. 2 and 3, angular sector $S_3$, emitting a blue radiation spectrum, is located on the same side, in relation to the axis of revolution X, as angular sector T3 of the finish surface from which the blue radiation spectrum is collected. The image formation system 6 thus forms an image by selecting the light rays returned for each angular sector of the surface to be inspected T, located on the same side as the angular sector of the lighting system.

According to this preferred implementation example, the device 1 of the invention is used to totally separate the components of the light called opposite and adjacent. In other words, the light beams returned by the surface to be inspected T, and intended to form the image, arrive only from the incident light beams coming from an adjacent lighting sector, that is located on the same side in relation to the axis of revolution X. Thus, the light rays returned by the finish surface T of a given sector do not return the light beams coming from an angular sector of the opposite light source, since the returned light rays are blocked by the filter. If we look at an angular sector ($T_1$ for example) illuminated in red for example, through the red filter $14_1$ and receiving no opposite light, namely green or blue, for the red sector, then only the red light adjacent to angular sector $T_1$ contributes to the image. The parasites coming from the beams opposite can therefore be removed, which provides better discrimination of the faults.

It should be noted that for certain applications, it is possible to envisage selecting only the light rays returned by the surface to be inspected T and coming from an angular sector of the lighting sector located on the side opposite, in relation to the axis of revolution X, to the angular sector of the said surface to be inspected. For example, in the example illustrated, it can be arranged that filter $15_1$, extending over angular sector $U_1$, allows transmission of the blue radiation spectrum which is emitted by angular sector S3 located on the side opposite, in relation to the axis of revolution X, to filter $15_1$.

The invention is not limited to the examples described and represented, since diverse modifications can be made to it without moving outside of its scope.

The invention claimed is:

1. An optoelectronic process for the inspection of an area of revolution (T) of a receptacle (3) presenting an axis of revolution (X), where the process includes the following steps:

illumination of the surface to be inspected (T) using a lighting system (5) presenting a lighting surface (S) with an axis of revolution (A) located in the extension of the axis of revolution (X) of the receptacle, and that includes at least three given radiation spectra separated from each other, formation of an image (I) of the surface to be inspected using a camera (7), for each angular sector ($T_1$, $T_2$, $T_3$) of the surface to be inspected by selecting only the light rays returned by the surface to be inspected and presenting one of the said given radiation spectra, so as to eliminate the parasitic light rays whose radiation spectrum does not correspond to that selected for the said angular sector, and analysis of the image formed with check the characteristics of the surface to be inspected, characterized in that it consists of:

illuminating the surface to be inspected (T) using the lighting system (5) whose the lighting surface (s) of revolution is divided over at least three angular sectors ($S_1$, $S_2$, $S_3$), each emitting a given radiation spectrum, so that at each point of the angular sectors ($S_1$, $S_2$, $S_3$) the radiation spectrum emitted is separate from the radiation spectrum emitted in the vicinity of a symmetrical point taken in relation to the axis of revolution (A).

2. A process according to claim 1, characterized in that it consists of forming an image for each angular sectors ($T_1$, $T_2$, $T_3$) of the surface to be inspected (T), by selecting only the light rays returned by the surface and coming from an angular sector ($S_1$, $S_2$, $S_3$) of the lighting system located on the same side as the said angular sector of the surface to be inspected in relation to the axis of revolution (X).

3. A process according to claim 1, characterized in that it consists of illuminating the surface to be inspected (T) in angular sectors of equal value.

4. A process according to claim 1, characterized in that it consists of illuminating by means of radiation spectra that are each of a given color.

5. A process according to claim 1, characterized in that it consists of analyzing the image formed in order to determine the flashing or surface faults of the finish of a receptacle.

6. An optoelectronic device for inspection of a surface of revolution (T) of a receptacle (3) presenting an axis of revolution (X), where the device includes:

a lighting system (5) presenting a lighting surface (S) with an axis of revolution (A) located in the extension of the axis of revolution (X) of the receptacle, and that includes at least three given radiation spectra separated from each other, and a system (6) to form an image (I) of the surface to be inspected, that includes a camera (7) and means (9) for analysis of the image with a view to checking the characteristics of the surface to be inspected, where the image formation system (6) forms an image for each angular sector ($T_1$, $T_2$, $T_3$) of the surface to be inspected by selecting only the light rays returned by the surface and presenting one of the said given radiation spectra, so as to eliminate the parasitic light rays whose radiation spectrum does not correspond to that selected for the said angular sector, characterized in that:

the lighting system (5) has a lighting surface of revolution (S) divided into at least three angular sectors ($S_1$, $S_2$, $S_3$), each emitting a given radiation spectrum, so that at each point of the angular sectors ($S_1$, $S_2$, $S_3$) the radiation spectrum emitted is separate from the radiation spectrum emitted in the vicinity of a symmetrical point taken in relation to the axis of revolution (A).

7. A device according to claim 6, characterized in that the image formation system (6) forms an image for each angular sector sectors ($T_1$, $T_2$, $T_3$) of the surface to be inspected by selecting only the light rays returned by the surface and coming from an angular sector ($S_1$, $S_2$, $S_3$) of the lighting system located on the same side as the said angular sector of the surface to be inspected in relation to the axis of revolution (X).

8. A device according to claim 6, characterized in that the lighting system (5) includes an annular source (13) that presents all of the given radiation spectra, and a series of at least three filters ($14_1$, $14_2$, $14_3$) located between the annular source (13) and the surface to be inspected (T), each lying on an angular sector ($S_1$, $S_2$, $S_3$), and each filter presenting a given transmission spectrum separated from that of the other filters.

9. A device according to claim 7, characterized in that the lighting system (5) includes a series of elementary light sources (10) divided over at least three angular sectors ($S_1$, $S_2$, $S_3$) and emitting a light spectrum that is different for each angular sector.

10. A device according to claim 6, characterized in that the image formation system (6) includes a series of at least three filters ($15_1$, $15_2$, $15_3$) interposed between the camera (7) and the surface to be inspected (T), each lying on an angular sector ($U_1$, $U_2$, $U_3$), each filter presenting a given transmission spectrum separated from that of the other filters.

11. A device according to claim 6, characterized in that the image formation system (6) includes means for processing the signals delivered by a color camera (7) so as to obtain, for each angular sector of the surface to be inspected ($T_1$, $T_2$, $T_3$), a signal that is representative of a given radiation spectrum.

* * * * *